(12) United States Patent
Daniel

(10) Patent No.: US 8,585,582 B2
(45) Date of Patent: *Nov. 19, 2013

(54) PERISTALTICALLY INFLATABLE PENILE PROSTHETIC

(71) Applicant: Coloplast A/S, Humlebaek (DK)

(72) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/680,126

(22) Filed: Nov. 19, 2012

(65) Prior Publication Data

US 2013/0079592 A1 Mar. 28, 2013

Related U.S. Application Data

(63) Continuation of application No. 13/043,483, filed on Mar. 9, 2011, now Pat. No. 8,343,033, which is a continuation of application No. 12/837,507, filed on Jul. 16, 2010.

(30) Foreign Application Priority Data

Jul. 15, 2010 (DK) .................................. 2010 70334

(51) Int. Cl.
*A61F 13/00* (2006.01)

(52) U.S. Cl.
USPC ........................................................... 600/40

(58) Field of Classification Search
USPC ..................................................... 600/38–41
See application file for complete search history.

(56) References Cited

U.S. PATENT DOCUMENTS

| | | | | |
|---|---|---|---|---|
| 4,009,711 A | * | 3/1977 | Uson | 600/40 |
| 4,360,010 A | * | 11/1982 | Finney | 600/40 |
| 4,898,158 A | * | 2/1990 | Daly et al. | 600/40 |
| 5,230,694 A | * | 7/1993 | Rosenblum | 600/40 |
| 8,343,033 B2 | * | 1/2013 | Daniel | 600/40 |

* cited by examiner

*Primary Examiner* — Samuel Gilbert
(74) *Attorney, Agent, or Firm* — Coloplast Corp., Coloplast A/S; Nick Baumann

(57) ABSTRACT

A penile prosthetic includes a proximal tip in communication with a reservoir, a cylinder bladder connected at a proximal end to the proximal tip and extending to a distal end, and peristaltic tubing disposed inside the cylinder bladder. The peristaltic tubing has a proximal end that communicates with the reservoir and a distal end that is open to the cylinder bladder. Peristaltic compression applied from the proximal end to the distal end of the peristaltic tubing pumps fluid from the reservoir into the cylinder bladder.

6 Claims, 12 Drawing Sheets

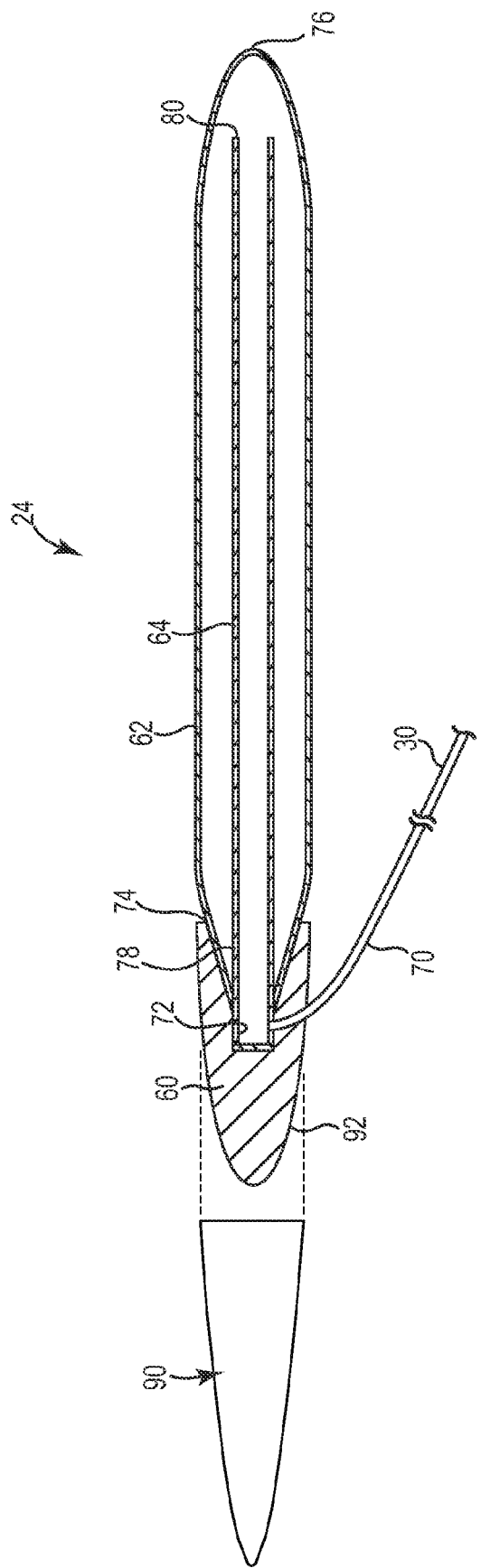

US 8,585,582 B2

PERISTALTICALLY INFLATABLE PENILE PROSTHETIC

BACKGROUND

An implanted penile prosthetic is effective in relieving erectile dysfunction in men.

A penile prosthetic typically includes a cylinder that is implanted in a corpora cavernosum of the penis, a liquid reservoir implanted in the abdomen that communicates with the cylinder(s), and a pump located in the scrotum that is employed to move liquid from the liquid reservoir into the cylinder(s).

In a typical application, the user squeezes a bulb of the pump multiple times to incrementally draw liquid out of the liquid reservoir, into the bulb, and eventually into the cylinders. The repeated squeezing of the bulb moves the liquid from the reservoir into the cylinders, which incrementally deflates the reservoir and incrementally inflates the cylinder(s) to eventually provide the user with an erect penis. The user may return the penis to its flaccid state by selectively transferring the liquid from the cylinder(s) back into the reservoir.

The above-described penile prosthetics have proven effective in relieving erectile dysfunction in men. However, surgeons and patients have expressed a desire for improved penile prostheses.

SUMMARY

One aspect provides a single monolithic pump with a fluid reservoir integrated in the pump, where the single monolithic pump/reservoir is implantable into a corpora cavernosum of the penis to treat erectile dysfunction.

One aspect provides a penile prosthetic that includes a proximal tip in communication with a reservoir, a cylinder bladder connected at a proximal end to the proximal tip and extending to a distal end, and peristaltic tubing disposed inside the cylinder bladder. The peristaltic tubing has a proximal end that communicates with the reservoir and a distal end that is open to the cylinder bladder. Peristaltic compression applied from the proximal end to the distal end of the peristaltic tubing pumps fluid from the reservoir into the cylinder bladder.

One aspect provides a method of treating erectile dysfunction. The method includes providing a pump having a proximal tip communicating with a fluid reservoir, a bladder connected at a proximal end to the proximal tip and extending to a closed distal end, and a tube disposed in the bladder, the tube having a proximal end in fluid communication with the fluid reservoir and a distal end that opens into the bladder. The method additionally includes implanting the pump into a corpora cavernosum of a penis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 4 is a cross-sectional side view of one embodiment of the pump illustrated in FIG. 1.

DETAILED DESCRIPTION

Figure 1:
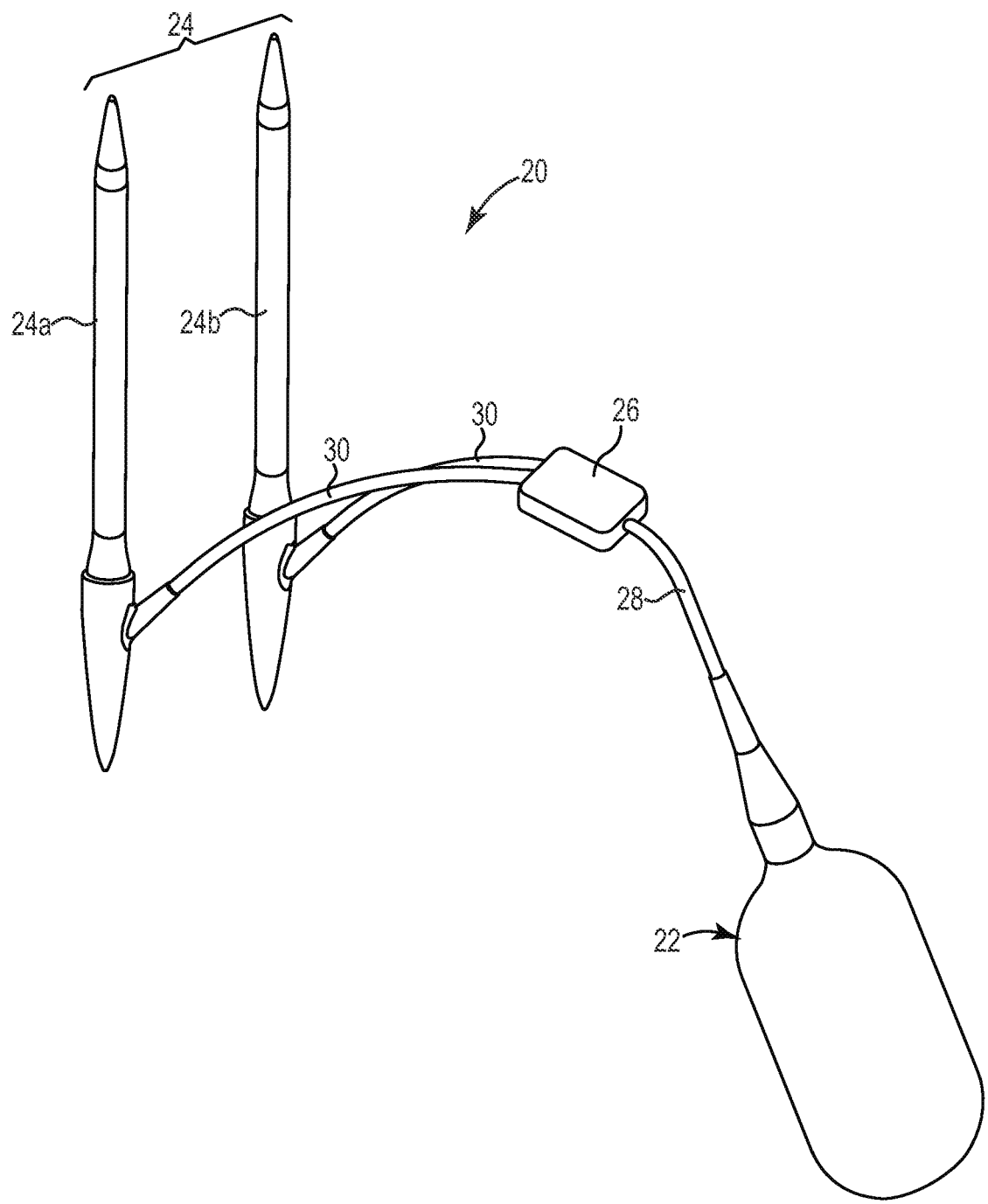
FIG. 1 is a perspective view of one embodiment of a penile prosthetic system including a pump that is implantable into a corpora cavernosum of a penis, a reservoir implantable into an abdomen, and a check valve connected between the pump and the reservoir.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

"Fluid" means a non-solid substance that flows and includes gases and liquids, or a combination of a gas and a liquid.

"Gas" means a substance having molecules that disperse and are free to expand to occupy an entire volume of a container in which it is disposed. Air and methyl butane are two examples of gases.

"Liquid" means a substance having molecules that do not disperse such that the liquid resists compression and the molecules of the liquid will not disperse to fill all spaces of a container in which the liquid is disposed. Saline is an example of a liquid.

Atmospheric pressure at sea level is approximately 14 pounds per square inch (PSI). The pressure measured or referred to as regards the pressurized liquid in the penile prosthetic assembly described herein is in reference to a gauge pressure, which is a pressure that has been increased above atmospheric pressure. This gauge pressure is recorded as pounds per square inch gauge (PSIg).

Peristaltic means a wavelike contraction of a tube or a tubular structure between an entrance opening and an exit opening by which contents in the tube are forced to the exit opening. Peristaltic compression is a wavelike contraction that is provided, in one example, by pinching the tube with fingers (or a device) and sliding the fingers/device from near the entrance opening toward the exit opening. Peristaltic compression is referred to as a moving compression.

Embodiments provide a pump that is implanted into a corpora cavernosum of the penis, where the pump includes a bladder and a tube disposed in the bladder. The tube is configured to peristaltically move fluid from a reservoir into the bladder. In one embodiment, the reservoir is implanted into the abdomen of the patient and the pump is implanted into the corpora cavernosum of the penis. In one embodiment, a single monolithic pump with a fluid reservoir integrated inside the pump is implantable into a corpora cavernosum of the penis. In various embodiments, the patient uses his fingers to initiate a wavelike contraction of the tube that peristaltically moves fluid from the reservoir into the bladder, thus inflating the bladder and creating an erection.

FIG. 1 is a perspective view of one embodiment of a penile prosthetic system 20. The penile prosthetic system 20 (system 20) includes a fluid reservoir 22, a pair of penile prosthetic pumps 24, and a check valve 26 connected between the fluid reservoir 22 and the penile prosthetic pumps 24. In one embodiment, the penile prosthetic pumps 24 includes a first prosthetic pump 24a that is implantable into a first corpora cavernosum of the penis and a second prosthetic pump 24b that is implantable into a second corpora cavernosum of the penis. The reservoir 22 is implantable in the body, for example within the abdomen of the user. Tubing 28 is connected between the fluid reservoir 22 and the check valve 26, and each of the prosthetic pumps 24 includes tubing 30 connected to the check valve 26. Thus, the pumps 24 communicated with the reservoir 22 via the tubing 28, 30.

Figure 2:
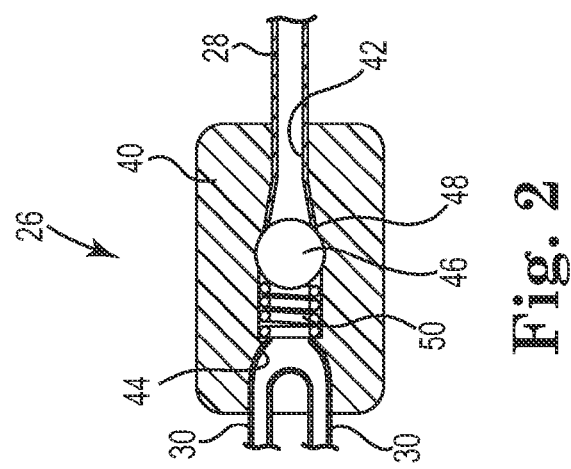
FIG. 2 is a cross-sectional top view of the check valve illustrated in FIG. 1.

FIG. 2 is a cross-sectional top view of one embodiment of the check valve 26. The check valve 26 includes a body 40, an inlet opening 42 and an outlet opening 44, and a ball 46 that is biased against a seat 48 by a spring 50. In one embodiment, the body 40 is a deformable body molded or otherwise fabricated from a resilient/compressible polymer such as silicone or a thermoplastic polymer.

Figure 3A:
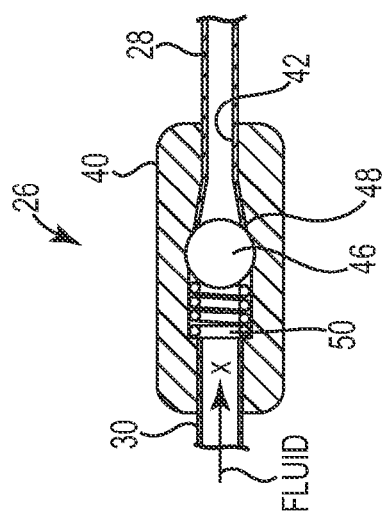
FIG. 3A is a cross-sectional side view of the check valve illustrated in FIG. 2 in a configuration that impedes fluid flow from the pump to the reservoir.

The check valve 26 is configured to allow fluid to be drawn from the reservoir 22 (FIG. 1) into the pumps 24 and impede or restrict the fluid from flowing out of the pumps 24 and back to the reservoir 22 until this flow condition is selectively permitted by the user (as illustrated in FIG. 3A).

During an exemplary inflation of the pumps 24, the fluid is moved through the tubing 28 and the inlet opening 42 by a pumping condition or a pressure condition that moves the fluid out of the reservoir 22 with a pressure sufficient to displace the ball 46 off of the seat 48. The fluid moves through the outlet opening 44 and the tubing 30 and into the penile prosthetic pumps 24 (FIG. 1).

FIG. 3A is a cross-sectional side view of the check valve 26 illustrating that the fluid inside of the penile prosthetic pumps 24 is prevented from flowing back through the check valve 26 by the spring 50 that biases the ball 46 against the seat 48. In this manner, the fluid employed to inflate the pumps 24 (FIG. 1) maintains the pumps 24 in the inflated state until the user selectively manipulates the check valve 26 to allow deflation of the pumps 24.

Figure 3B:
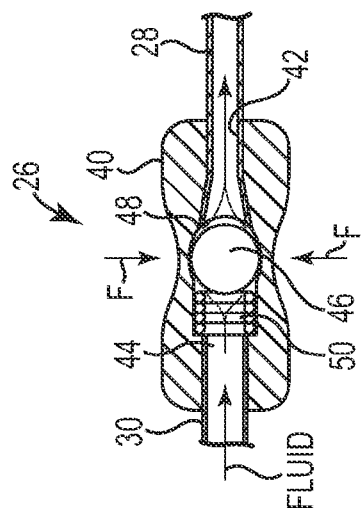
FIG. 3B is a cross-sectional side view of the check valve in a configuration that allows the fluid to flow from the pump to the reservoir.

FIG. 3B is a cross-sectional side view of the check valve 26 illustrating user-manipulation of the check valve 26 to allow deflation of the pumps 24. In one embodiment, the user-manipulation of the check valve 26 includes an application of a force F to deform the body 40. Deformation of the body 40 results in the ball 46 being displaced off of the seat 48, which allows the fluid to flow from the outlet opening 44 past the ball 46 and back through the inlet opening 42 to the reservoir 22 (FIG. 1).

FIG. 4 is a cross-sectional side view of one embodiment of the penile prosthetic pump 24. One of the penile prosthetic pumps 24 is described with the understanding that the typical application would include two implanted pumps 24, one in each of the two corpora cavernosa of the patient.

The penile prosthetic pump 24 includes a proximal tip 60, a cylinder bladder 62 connected to the proximal tip 60, and peristaltic tubing 64 disposed inside of the cylinder bladder 62. The penile prosthetic pump 24 is illustrated with the cylinder bladder 62 offset from the peristaltic tubing 64 for improved descriptive clarity, although it is to be understood that a flaccid pump 24 (e.g., a pump 24 that is not fully inflated) would have the bladder 62 relaxed in a wrinkled or crumpled state where the bladder 62 might even contact the peristaltic tubing 64.

The proximal tip 60 communicates with the reservoir 22 (FIG. 1) via a conduit 70. In one embodiment, the proximal tip 60 is a substantially solid proximal tip that is formed to provide a chamber 72, with the conduit 70 extending from the chamber 72 to the reservoir 22 and the peristaltic tubing 64 communicating with and extending from the chamber 72.

The cylinder bladder 62 extends from a proximal end of 74 that is connected to the proximal tip 60 distally to a closed distal end 76. In one embodiment, the cylinder bladder 62 is provided as a sealed and substantially enclosed bladder that defines a lumen, and the peristaltic tubing 64 is disposed inside of the lumen.

The peristaltic tubing 64 has a proximal end 78 that is connected with the chamber 72 and a distal end 80 that opens into the cylinder bladder 62. In one embodiment, the peristaltic tubing 64 is a cantilevered tube with the proximal end 78 connected to the proximal tip 60 and the distal end 80 free and unsupported, where the distal end 80 opens into the cylinder bladder 62. Peristaltic compression applied from the proximal end 78 toward the distal end 80 of the peristaltic tubing 64 pumps fluid from the reservoir 22 (FIG. 1) into the cylinder bladder 62.

In one embodiment, an optional rear tip extender 90 is provided that is attachable to a proximal end portion 92 of the proximal tip 60. The overall length of a penis includes an internal body portion located at a proximal end (termed the crus of the penis) to an external distal end (termed the glans penis). Naturally, the length of the penis differs between patients. The optional rear tip extender 90 is provided to extend the penile prosthetic pump 24 a greater distance in the proximal direction, which allows the penile prosthetic to extend into the crus of the penis for an improved fit.

In one embodiment, the penile prosthetic 24 is substantially cylindrical or otherwise suited to be implantable into a corpora cavernosum of the penis and includes the conduit 70 extending from the proximal tip 60, with the bladder 62 connected to the proximal tip 60, and the peristaltic tubing 64 is operable as a peristaltic pump and disposed in the bladder 62. Sliding wave-like compression applied from the proximal end 78 to the distal end 80 of the peristaltic pump 64 moves the fluid from the fluid reservoir 22 into the bladder 62.

Suitable materials for fabricating the penile prosthetic pump 24 include polymers, with two examples being polyurethane or silicone. For example, in one embodiment the bladder 62 is fabricated from a urethane material sold under the trademark BIOFLEX available from Coloplast Corp., Minneapolis, Minn. and the distal end 76 of the bladder 62 is subsequently dipped in additional urethane material that cures to provide a desirable leading-end shape to the bladder 62. In one embodiment, the bladder 62 is formed from silicone, which is dissimilar to urethane. To facilitate the attachment of these two dissimilar materials, in one embodiment the silicone bladder is coated with fumed silica to prepare the surface for bonding with a urethane distal end tip.

Figure 5:
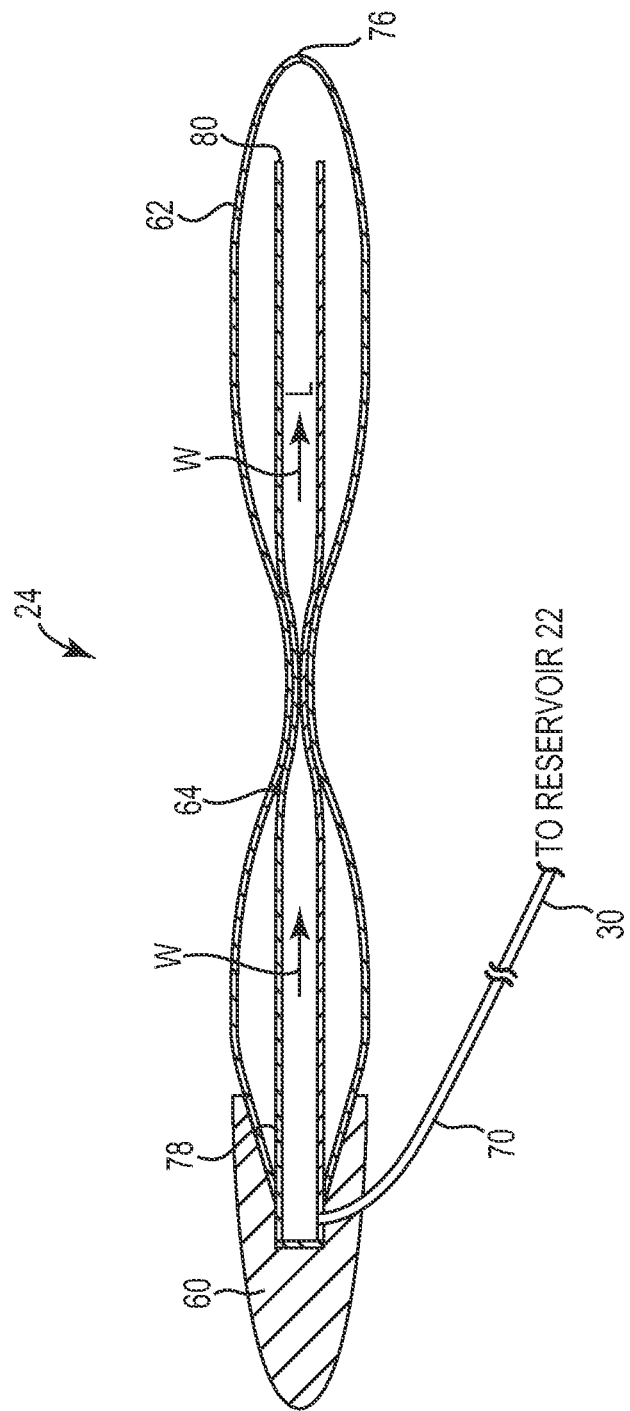
FIG. 5 is a cross-sectional side view of the pump illustrated in FIG. 4 peristaltically compressed to drive the fluid into a bladder of the pump.

FIG. 5 is a cross-sectional side view of the pump 24 peristaltically compressed to draw fluid L from the reservoir 22 into the bladder 62 to inflate the penile prosthetic pump 24. In one embodiment, the user compresses the bladder 62 and squeezes the walls of the peristaltic tubing 64 together, and while squeezing the walls of the peristaltic tubing 64, slides the compression from the proximal end 78 toward the distal end 80 of the tubing 64. The moving compression of the peristaltic wave W suctions the fluid L from the reservoir 22, through the conduit 70, and passes the fluid L through the peristaltic tubing 64 into the bladder 62. Subsequent, repeated moving compressions of the peristaltic wave W will drive more fluid L into the bladder 62

Figure 6:
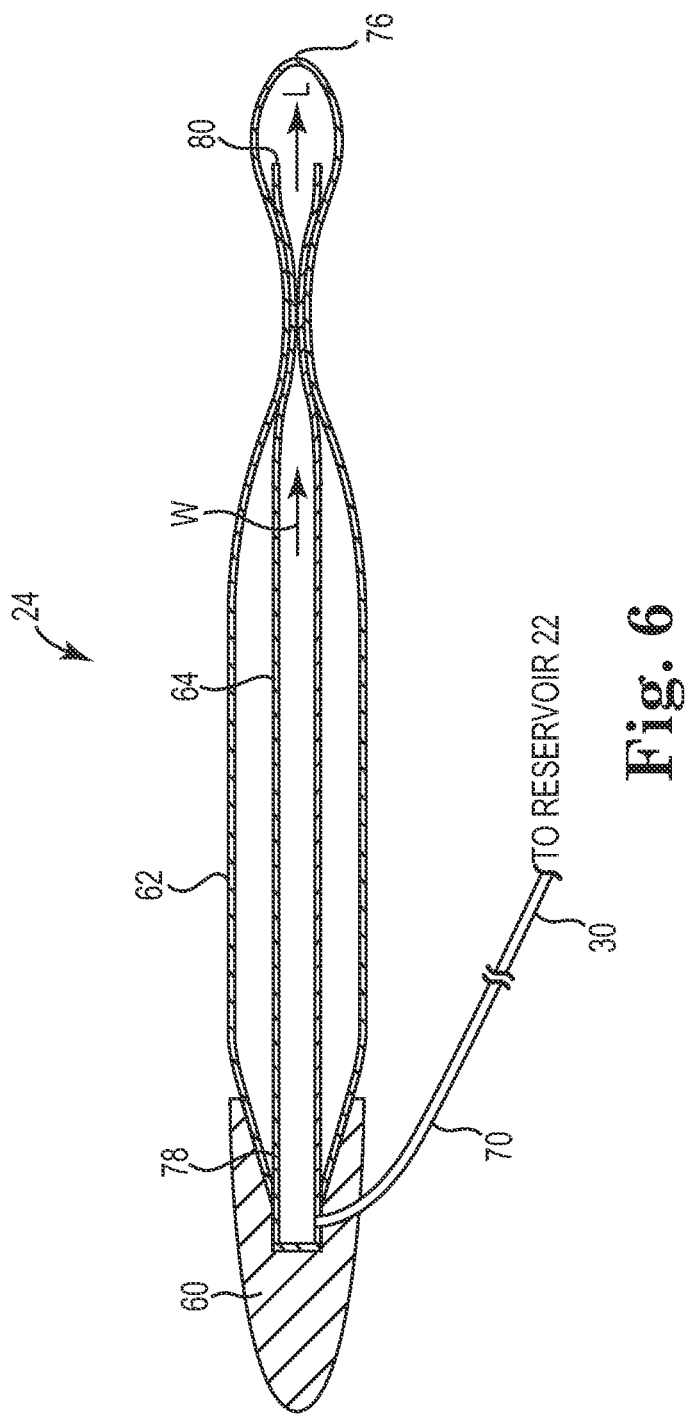
FIG. 6 is a cross-sectional side view of the pump illustrated in FIG. 5 further peristaltically compressed to drive additional fluid into the bladder of the pump.

FIG. 6 is a cross-sectional side view of the pump 24 further peristaltically compressed to pass the fluid L into the bladder 62. The moving compression has moved from the central section of the cylinder bladder 62 toward the distal end 76, thus moving the fluid L to the free end 80 of the tubing 64 and ejecting the fluid L into the cylinder bladder 62. In one embodiment, the user is instructed by the surgeon to eject the fluid L out of the peristaltic tubing 64 into the cylinder bladder 62 until the bladder 62 is pressurized to about 10-20 PSIg.

Figure 7:
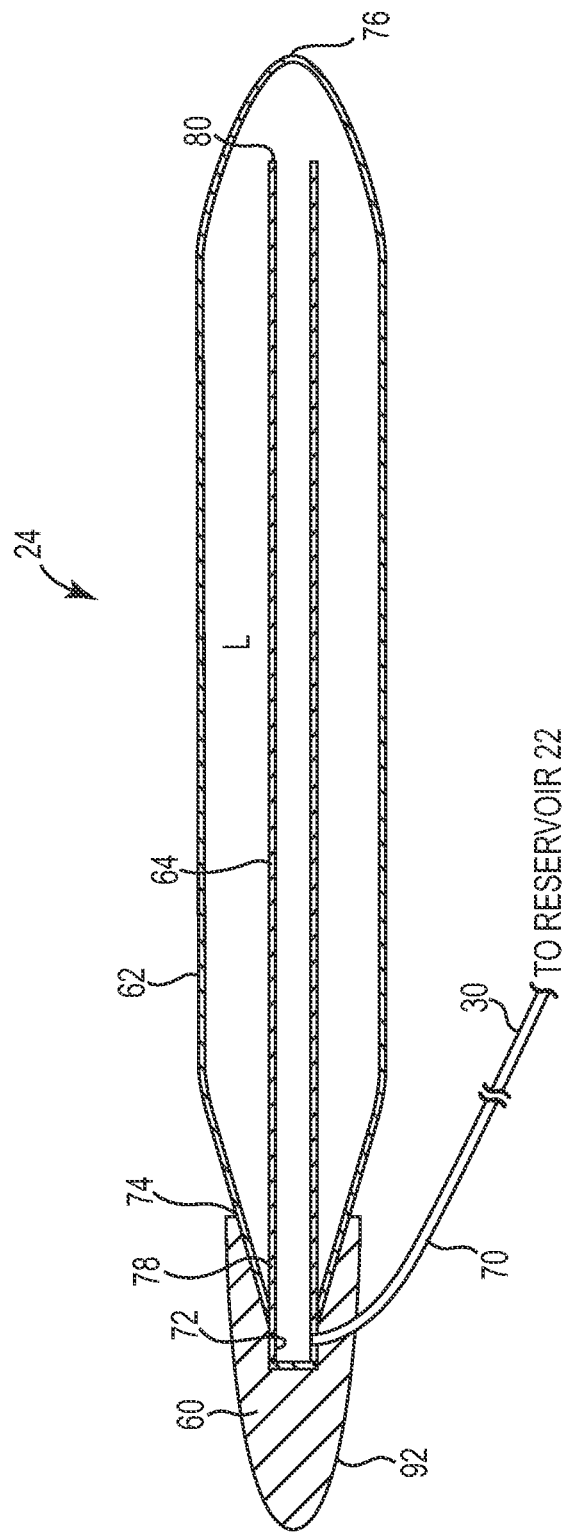
FIG. 7 is a cross-sectional side view of the pump illustrated in FIG. 4 after peristaltic inflation of the bladder.

FIG. 7 is a cross-sectional side view of the penile prosthetic pump 24 fully inflated after application of peristaltic compression to the peristaltic tubing 64. The fluid L has been peristaltically pumped from the reservoir 22 through the peristaltic tubing 64 and into the cylinder bladder 62. The check valve 26 (FIG. 3A) impedes the flow of the fluid L out of the cylinder bladder 62, which allows the penile prosthetic pump 24 to maintain its inflation pressure until the user selectively activates the check valve 26 to drain the fluid L from the cylinder bladder 62 back into the reservoir 22. In one embodiment, the fluid L in the cylinder bladder 62 is pressurized to about 10-20 PSIg by the pumping of the peristaltic tubing 64.

Figure 8:
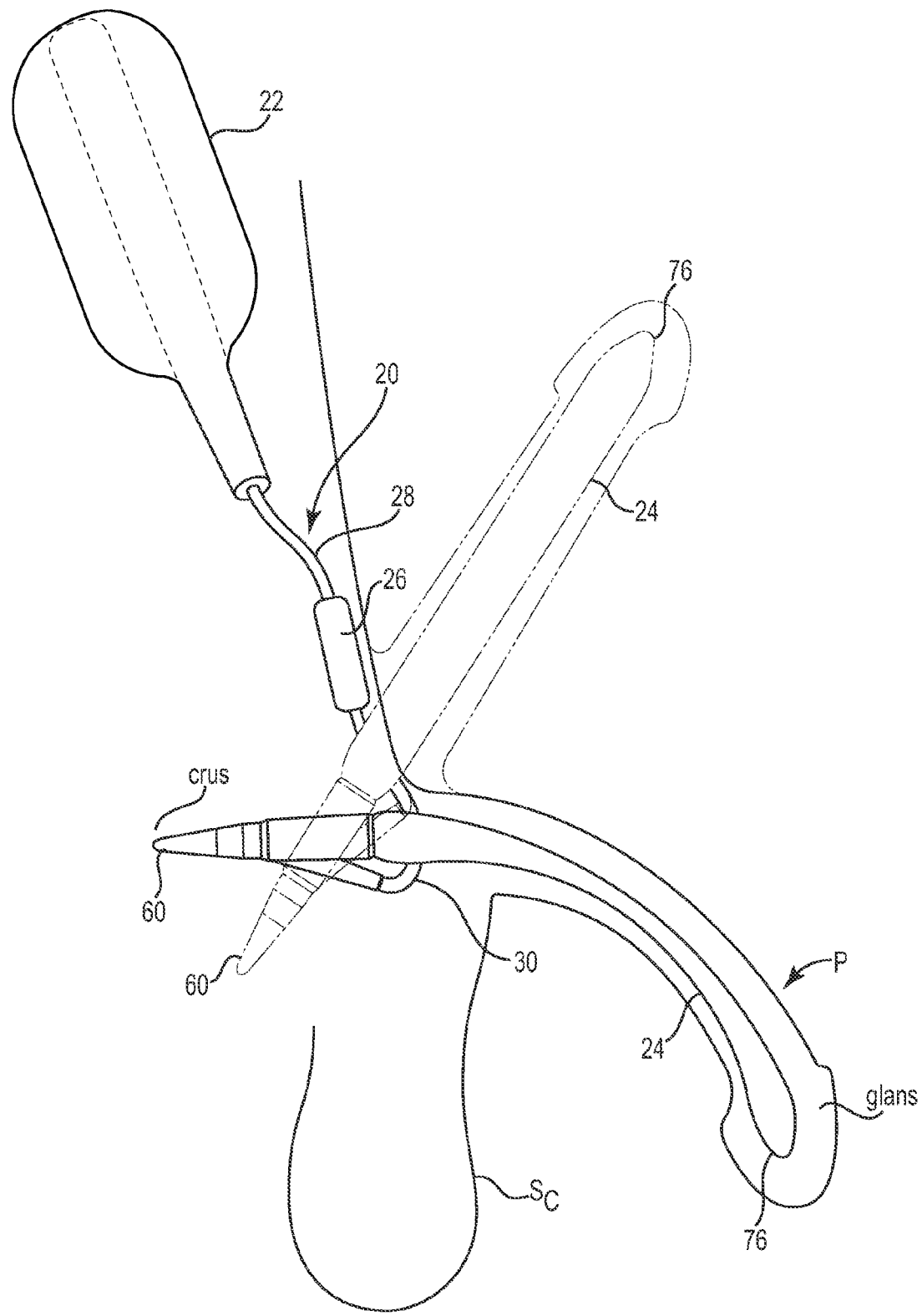
FIG. 8 is a schematic view of the penile prosthetic system illustrated in FIG. 1 with a pair of pumps implanted into the corpora cavernosa of the penis.

FIG. 8 is a schematic view of the penile prosthetic system 20 with the reservoir 22 implanted in the patient's abdomen and a prosthetic pump 24 implanted into each corpora cavernosum of the penis P.

In one exemplary implantation approach, the groin area of the patient is cleaned, shaved, and suitably prepped with, for example, a surgical solution prior to draping with a sterile drape. A retraction device, such as a retractor sold under the trademark LONE STAR available from Lone Star Medical Products of Stafford, Tex., is placed around the penis P. Thereafter, the surgeon forms an incision to access the corpora cavernosum of the patient, where suitable examples of incisions include either an infrapubic incision or a transverse scrotal incision.

The infrapubic incision is initiated between the umbilicus and the penis (i.e., above the penis), whereas the transverse scrotal incision is made across an upper portion of the patient's scrotum Sc. As an example of the transverse scrotal approach, the surgeon forms a 2-3 cm transverse incision through the subcutaneous tissue of the median raphe of the upper scrotum Sc and dissects down through the Dartos fascia and Buck's fascia to expose the tunicae albuginea of the penis P.

Thereafter, each corpora cavernosum is exposed in a corporotomy where a small (approximately 1.5 cm) incision is formed to allow the surgeon to access and dilate the corpora cavernosum. The corpora cavernosum is dilated distally toward the glans and proximally toward the crus with a suitable tool to create a space for the penile prosthetic pump 24. For example, the surgeon begins dilation of both the distal and proximal corpora cavernosum by introducing an 8 mm dilator into the spongy tissue of the corpora with sequential progression to about a 14 mm dilator, each of which are introduced and pushed distally toward the glans penis and proximally toward the crus of the penis. The surgeon measures a length of the dilated corpora cavernosum to facilitate selection of the proper length of the penile prosthetic pump 24 and adjusts the length of the implant by adding an appropriately sized rear tip extender 90 (FIG. 4) as desired.

After dilation of the corpora cavernosa, a deflated penile prosthetic pump 24 (FIG. 4) is inserted into the prepared corporotomy. The surgeon may palpate the end of penis P at the subcoronal area to locate the distal end 76 of the penile prosthetic pump 24 to ensure proper interior placement of the prosthesis in the patient.

The reservoir 22 is connected to the penile prosthetic pump 24 via the tubing 28, 30 and the surgeon inflates and deflates the bladder 62 to ensure proper function of the system 20. Thereafter, a reservoir 22 filled with fluid L is implanted into the abdomen, for example in the space of Retzius, and the surgical site is closed to allow the patient to heal.

During use, and with reference to FIGS. 5-7, the patient will apply peristaltic compression to the peristaltic tubing 64 from a location adjacent to the proximal end 78 of the peristaltic tubing 64 toward the distal end 80 of the peristaltic tubing 64 to draw fluid from the reservoir 22 into the cylinder bladder 62 to inflate the penis from a flaccid state to an erect state. The check valve 26 is configured to allow the fluid to flow from the reservoir 22 into the peristaltic pump 24 implanted in the penis P to inflate the cylinder bladder 62. The check valve 26 is configured as a one-way valve that impedes or prevents the return flow of the fluid L from the peristaltic pump 24 back into the reservoir 22 until the patient selectively and manually manipulates the check valve 26 to allow the return flow of the fluid.

The peristaltic pump 24 allows the patient improved control in transitioning the penis from its flaccid state to the erect state by manually initiating a wavelike contraction in the peristaltic tubing 64. Other devices for treating erectile dysfunction include a bulb pump, often located in the scrotum Sc. Manually pumping the bulb pump can be tiresome (especially for users with arthritis of the fingers), and has the potential to cause trauma to the skin of the scrotum Sc. In contrast, the peristaltic pump 24 of system 20 provides a more naturally-activated, controlled erection of the penis P.

Figure 9:
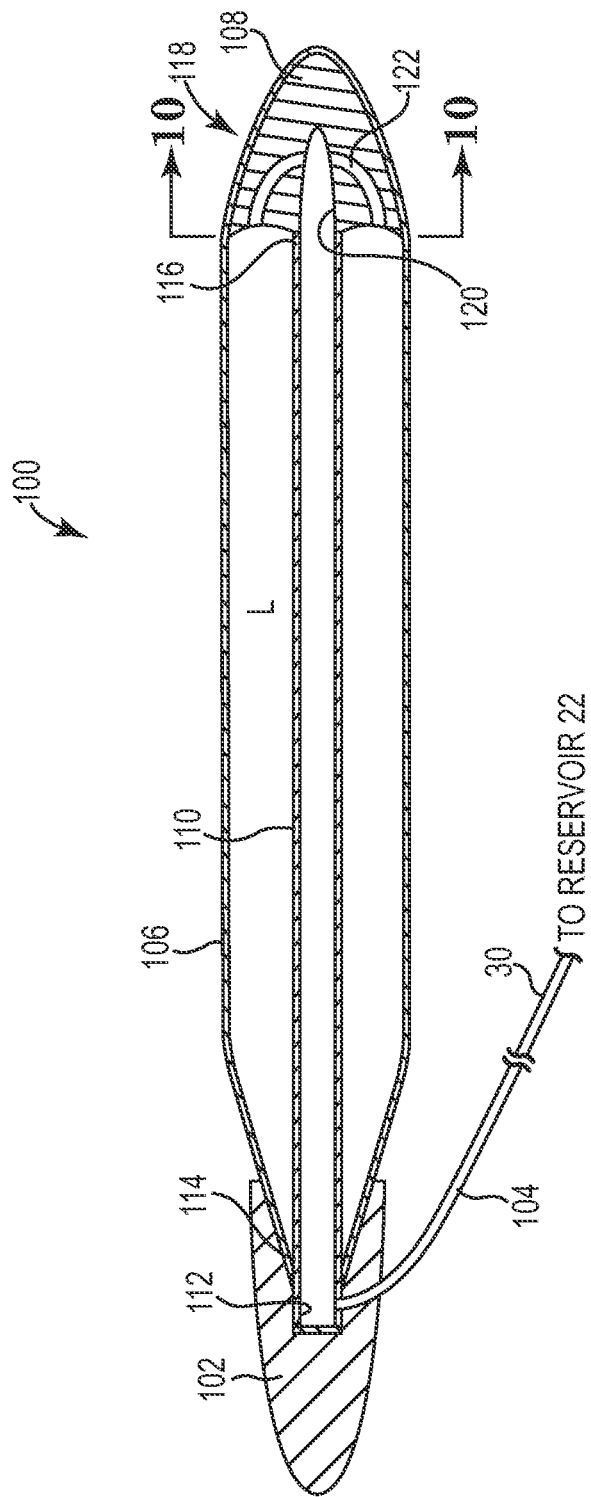
FIG. 9 is a cross-sectional side view of one embodiment of a pump configured to be implanted into a corpora cavernosum of a penis.

FIG. 9 is a cross-sectional side view of one embodiment of a peristaltic pump 100 suitable as an implantable penile prosthetic. In one embodiment, the peristaltic pump 100 (pump 100) includes a proximal tip 102 having a conduit 104 that communicates with the reservoir 22 (FIG. 1), a cylinder bladder 106 attached to the proximal tip 102 and including a manifold 108, and peristaltic tubing 110 extending between the proximal tip 102 and the manifold 108. The pump 100 is illustrated for descriptive purposes in an inflated state with the fluid L filling the bladder 106 to an erect state.

The conduit 104 is similar to the conduit 70 (FIG. 4) and is provided as tubing that is suitable for connection to the check valve 26 and the reservoir 22 illustrated in FIG. 1.

In one embodiment, the proximal tip 102 is formed to define a chamber 112, with the peristaltic tubing 110 connected to the chamber 112 at a proximal end 114 and connected to the manifold 108 at a distal end 116. In this embodiment, the peristaltic tubing 110 is supported and secured on both of its opposing ends 114, 116.

In one embodiment, the bladder 106 is a resilient and flexible bladder (similar to the bladder 62 described above in FIG. 4) and is configured to be inflated and deflated by a fluid that is pumped through the peristaltic tubing 110 into the manifold 108 to fill and inflate the bladder 106. The bladder 106 is suitably attached to the proximal tip 102 by adhesive, molding, sonic welding or other suitable attachment approaches for connecting two polymeric materials.

Figure 10:
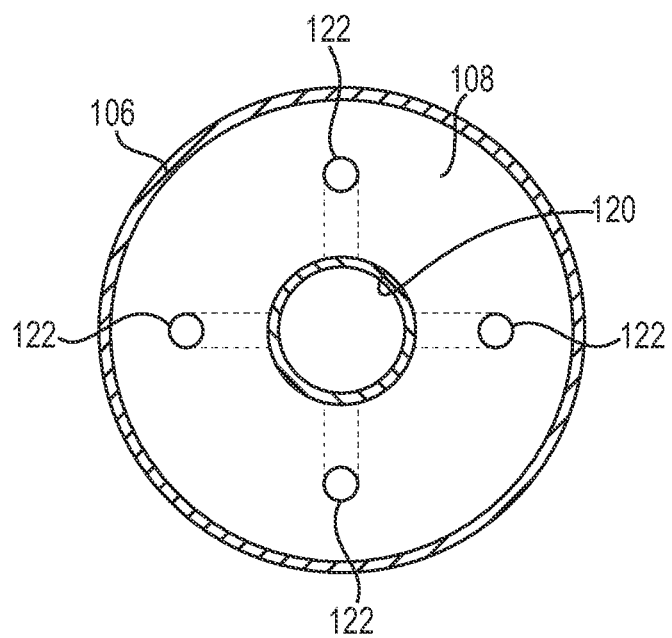
FIG. 10 is a front view of a manifold that is disposed in a distal end portion of the pump illustrated in FIG. 9.

FIG. 10 is a front view of the manifold 108 as disposed in a distal end portion 118 of the bladder 106. In one embodiment, the manifold 108 includes a central collector channel 120 that extends from the distal end 116 of the peristaltic the tubing 110 to communicate with one or more radial channels 122 that communicate between the central collector channel 120 and the cylinder bladder 106.

In one embodiment, the manifold 108 is provided as a relatively "soft" polymer, such as silicone with a durometer of less than about 30 Shore A, selected to provide a suitable soft and dexterous feel at the distal end portion 118 of the bladder 106. In one embodiment, the manifold 108 is provided as a firmer polymer, such as silicone with a durometer of more than about 30 Shore A, which provides a firmer tip at the distal end portion 118 of the bladder 106.

In one embodiment, the manifold 108 is formed to include one channel 122 that directs the fluid L from the peristaltic tubing 110 into the bladder 106. In one embodiment, the manifold 108 is formed to include multiple "shower head" channels 122 that direct the fluid L from the peristaltic tubing 110 into the bladder 106.

Figure 11:
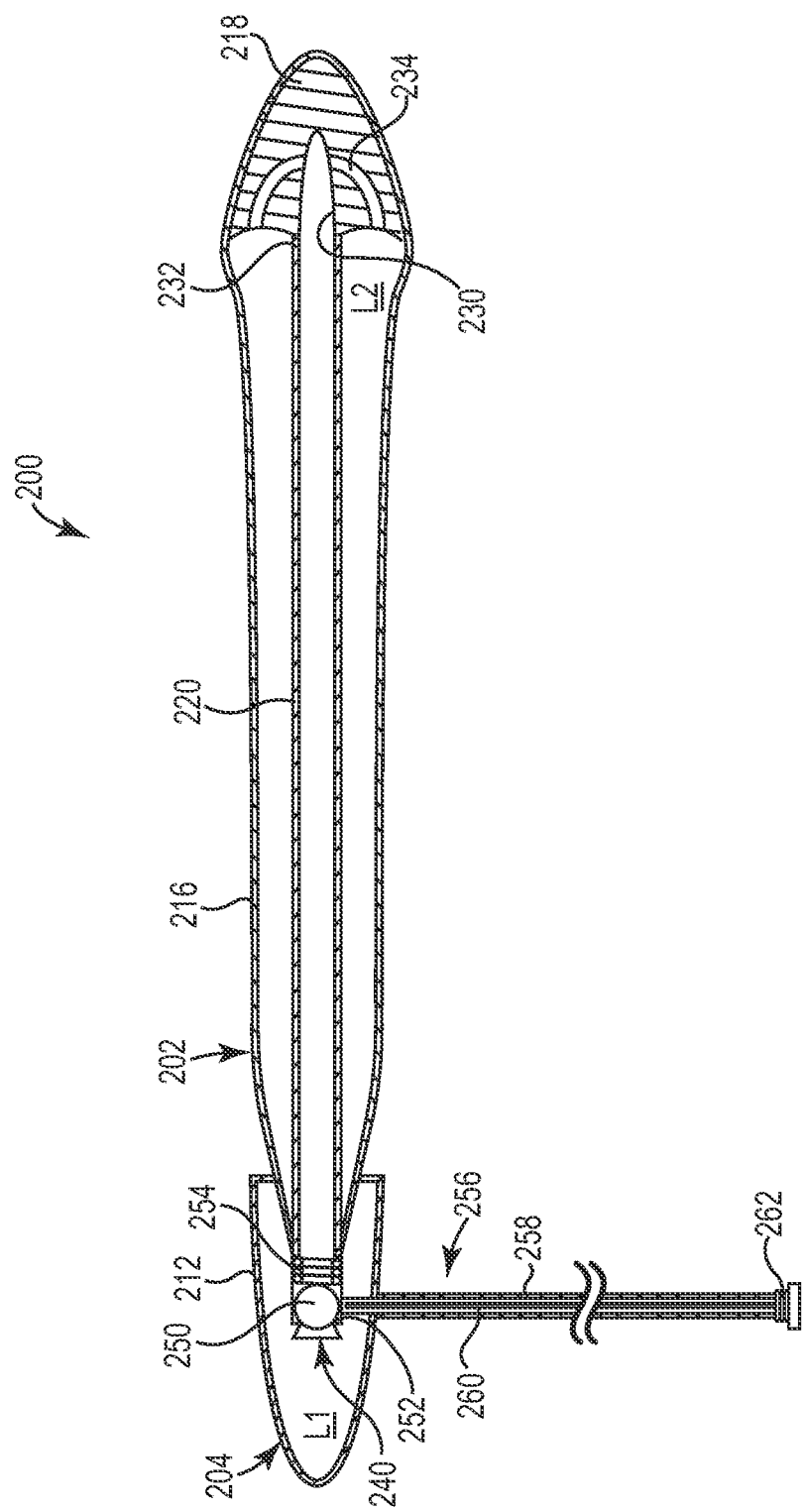
FIG. 11 is a cross-sectional side view of one embodiment of a penile implant monolithically formed to include a peristaltic pump and a fluid reservoir that are both implantable into a single corpora cavernosum of a penis.

FIG. 11 is a cross-sectional side view of one embodiment of a penile implant 200 including a peristaltic pump 202 and a fluid reservoir 204 that are both implantable into a single corpora cavernosum of a penis. In contrast to multi-component penile prosthetics that provide a fluid reservoir (usually implanted in the abdomen) separate from a fluid pump (usually implanted in the scrotum) with both the pump and the reservoir separate from the penile cylinders, the penile prosthetic implant 200 provides a single monolithic implant that includes the pump 202, the reservoir 204, and a girth-expanding bladder 216 all integrated into one device that is implantable into a corpora cavernosum of the penis.

In one embodiment, the peristaltic pump 202 (pump 202) includes a proximal tip 212 integrally formed to include the reservoir 204, a cylinder bladder 216 attached to the proximal tip 212 and including a manifold 218, and peristaltic tubing 220 extending between the proximal tip 212 and the manifold 218. The pump 202 is illustrated for descriptive purposes in a deflated state with a portion L1 of the total fluid volume of the implant 200 retained in the fluid reservoir 204 and a portion L2 of the total fluid volume of the implant 200 retained in the bladder 216. The peristaltic tubing 220 is operable to displace the portion L1 of the fluid retained in the fluid reservoir 204 into the bladder 216 so that the bladder 216 is inflated/pressurized by the combination of the fluid portion L1 and the fluid portion L2.

In one embodiment, the bladder 216 is a resilient and flexible bladder similar to the bladders described above and is configured to be inflated by pumping fluid through the peristaltic tubing 220 and the manifold 218 to fill and inflate the bladder 216. The bladder 216 is suitably attached to the proximal tip 212 by adhesive, molding, sonic welding or other suitable attachment approaches for connecting two polymeric materials.

In one embodiment, the manifold 218 is similar to the manifold 108 described above and includes a central collector channel 230 that extends from a distal end 232 of the peristaltic the tubing 220 to communicate with one or more radial channels 234 that communicate between the central collector channel 230 and the cylinder bladder 216. The fluid L1 that is pumped through the peristaltic tubing 220 is sprayed or distributed by the radial channels 234 into the bladder 216.

In one embodiment, the proximal tip 212 houses the reservoir 204 and a check valve assembly 240 that is disposed between the fluid reservoir 204 and the penile pump 202. The check valve assembly 240 is operable to separate the fluid L1 in the reservoir 204 from the fluid L2 in the bladder 216 when the pump 202 is in a deflated state. In addition, the check valve assembly 240 is operable by the user to selectively to deflate the bladder 216 by allowing the fluid L1 that is pumped into the bladder 216 to be returned into the reservoir 204.

In one embodiment, the proximal tip 212 is fabricated from stainless steel to provide a housing for the reservoir 204 and the check valve assembly 240.

In one embodiment, the check valve assembly 240 includes a ball 250 that is biased against a seat 252 by a spring 254 and a deflation mechanism 256 that is operable to displace the ball 250 off of the seat 252. In one embodiment, the deflation mechanism 256 is provided as a flexible plunger cable 256 including a plunger rod 260 retained within a cable 258 and biased in a spring-loaded manner by a spring 262. The plunger rod 260 is movable to displace the ball 250 off of the seat 252. In addition, the plunger rod is biased by the spring 262 to allow the ball 250 to remain on the seat 252 until the user selectively decides to deflate the bladder 216.

In one embodiment, the deflation mechanism 256 is provided as a flexible cable that is sized and configured for placement within the patient's scrotum. In other embodiments, the deflation mechanism 256 is suitably implanted in the abdomen or another body cavity of the patient. In one embodiment, the deflation mechanism 256 is surgically implanted within the patient's scrotum and connected to the monolithic unit of the pump 202 and the reservoir 204 that are both implanted within a corpora cavernosum of the penis.

Figure 12:
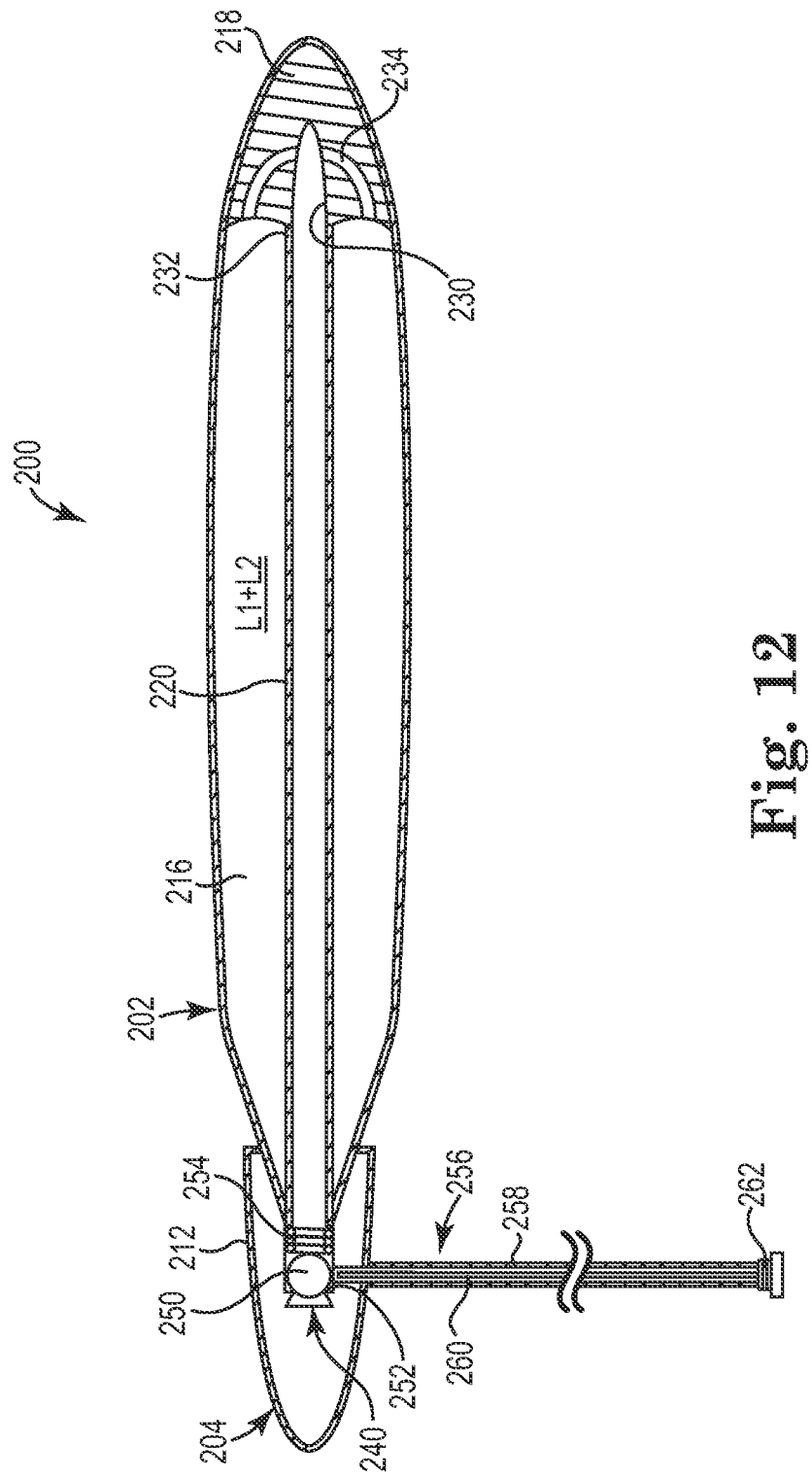
FIG. 12 is a cross-sectional side view of the penile implant illustrated in FIG. 11 in an inflated state.
Figure 13:
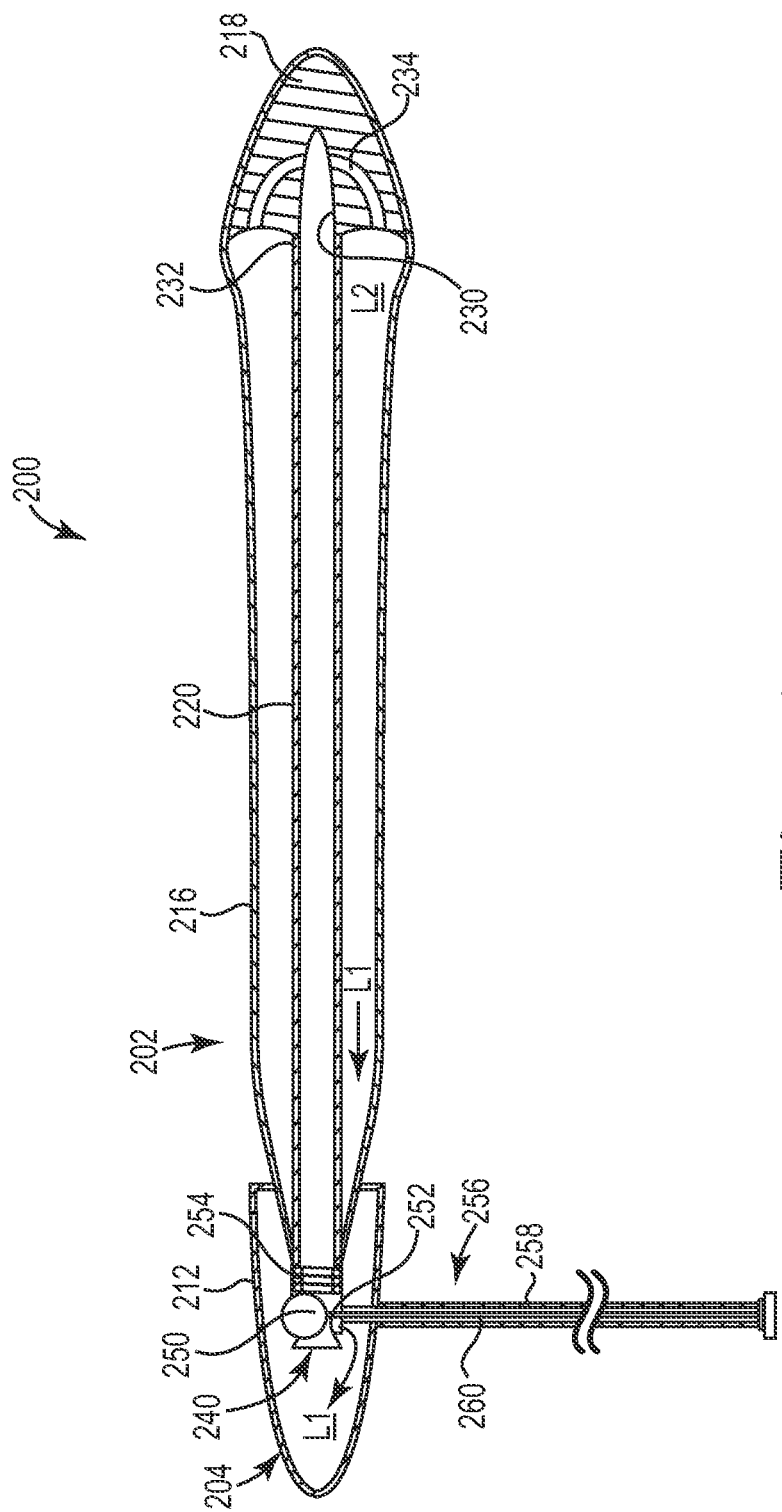
FIG. 13 is a cross-sectional side view of the penile implant illustrated in FIG. 11 in a deflated state.

FIG. 12 is a cross-sectional side view of the penile implant 200 in an inflated state and FIG. 13 is a cross-sectional side view of the penile prosthetic implant 200 in a deflated state.

FIG. 12 is a cross-sectional view of the penile implant 200 after the peristaltic tubing 220 has been peristaltically pumped to transfer the fluid L1 from the reservoir 204 into the bladder 216. The peristaltic pumping (See FIGS. 5 and 6) of the peristaltic tubing 220 suctions or draws the fluid L1 from the reservoir 204 with a sufficient pressure to compress the spring 254 and displace the ball 250 off of the seat 252, which results in the fluid L1 moving through the peristaltic tubing 220 into the bladder 216. The fluid portion L1 mixes with the fluid portion L2 to inflate the bladder 216 to a pressure of about 15 PSIg. The fluid in the bladder 216 is prevented from flowing back into the reservoir 200 by the ball 250 that is seated against the seat 252.

The portion of fluid L1 in addition to the portion of fluid L2 combine to provide a total volume of liquid that is selected to completely inflate the bladder 216. In one embodiment, the portion of fluid L1 has a volume of about 150 mL and the portion of fluid L2 as a volume of about 100 mL.

FIG. 13 is a cross-sectional side view of the penile prosthetic implant 208 in a deflated state. The plunger rod 260 has been pressed to displace the ball 250 off seat of the seat 252. A portion of the fluid L1 inside of the bladder 216 flows past the seat 252 and back into the reservoir 204, deflating the bladder 216. The user may assist the deflation of the bladder 216 by squeezing the bladder 216 while activating the plunger at 260. The plunger rod 260 is biased back into its stable configuration when deactivated by the user, allowing the ball 250 to return to the seat 252.

Embodiments provide a pump that is implanted into a corpora cavernosum of the penis, where the pump includes a peristaltic tube. The patient uses his fingers to initiate a wave-like contraction of the tube that peristaltically moves fluid from a reservoir into a bladder of the pump, thus inflating the bladder and creating an erection.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A penile prosthetic system comprising:
    a reservoir;
    a bladder attachable to communicate with the reservoir;
    tubing disposed inside the bladder, the tubing having one end that communicates with the reservoir and a second end that opens into the bladder; and
    a check valve connected between the reservoir and the tubing, the check valve configured to allow fluid to be drawn from the reservoir into the tubing and restrict the fluid from flowing out of the tubing and back to the reservoir;
    wherein the bladder is provided as a sealed and substantially enclosed lumen and the tubing is peristaltic tubing is disposed inside the sealed and substantially enclosed lumen.

2. The penile prosthetic system of claim 1, further comprising a manifold disposed at a distal end portion of the bladder, the manifold defining at least one channel extending from a distal end of the tubing to the bladder.

3. The penile prosthetic system of claim 1, wherein the tubing is cantilevered with a proximal end of the tube connected to a proximal tip of the penile prosthetic and a distal end of the tube is a free end.

4. A penile prosthetic that is inflatable with fluid contained in a reservoir, the penile prosthetic comprising:
    a bladder and a tube disposed inside the bladder, the tube having a proximal end that communicates with the reservoir and a distal end that opens into the bladder; and
    a check valve connected between the reservoir and the tube, the check valve configured to allow liquid to be drawn from the reservoir into the tube and restrict the liquid from flowing out of the tube and back to the reservoir;
    wherein the tube is configured to pump the liquid from the reservoir in response to compression applied from the proximal end of the tube to the distal end of the tube.

5. The penile prosthetic of claim 4, further comprising:
    a manifold disposed in a distal end portion of the bladder, the manifold having a channel communicating between the distal end of the tube and the bladder.

6. The penile prosthetic of claim 5, wherein the proximal end of the tube is connected to a proximal tip of the penile prosthetic and the distal end of the tube is connected to the manifold.

* * * * *